United States Patent [19]

Parish et al.

[11] Patent Number: 4,677,120

[45] Date of Patent: Jun. 30, 1987

[54] TOPICAL PRODRUGS FOR TREATMENT OF ACNE AND SKIN DISEASES

[75] Inventors: Harlie A. Parish; William P. Purcell, both of Memphis, Tenn.

[73] Assignee: Molecular Design International, Memphis, Tenn.

[21] Appl. No.: 760,881

[22] Filed: Jul. 31, 1985

[51] Int. Cl.[4] .......................... A61K 31/23; C11C 3/02
[52] U.S. Cl. ............................ 514/549; 260/410.9 V; 514/350; 514/423; 514/425; 514/461; 514/547; 546/314; 548/530; 549/255; 549/488
[58] Field of Search ............... 260/410.9 V; 514/350, 514/425, 423, 461, 547, 549; 546/314; 548/530; 549/255, 488

[56] References Cited

U.S. PATENT DOCUMENTS

| | | | |
|---|---|---|---|
| 3,287,382 | 11/1966 | van Leeuwen | 260/410.9 V |
| 3,928,400 | 12/1975 | Olson et al. | 260/410.9 V |
| 3,931,257 | 1/1976 | Pawson | 260/408 |
| 4,529,600 | 7/1985 | Dawson et al. | 514/529 |

*Primary Examiner*—Werren B. Lone
*Assistant Examiner*—Vera C. Clarke
*Attorney, Agent, or Firm*—James S. Waldron

[57] ABSTRACT

Esters and amides of 13-cis-retinoic acid are disclosed which are used for the treatment of acne and skin diseases.

14 Claims, No Drawings

TOPICAL PRODRUGS FOR TREATMENT OF ACNE AND SKIN DISEASES

BACKGROUND OF THE INVENTION

1. Field of the Invention

Retinol (vitamin A) and retinoic acid (vitamin A acid), its isomers, and certain of its analogs are known to have beneficial effects in the treatment of acne and keratinizing skin disorders.

Acne affects large patient populations and is a common inflammatory skin disorder which usually localizes on the face. Fortunately, the disease usually disappears and in the interval of months or years between onset and resolution, therapy, although not curative, can satisfactorily suppress the disease in the majority of patients.

A small number of acne patients with severe disease show little or no response to intensive therapeutic efforts including the use of high doses of oral tetracyline, dapsone, prednisone and, in women, estrogen. In many cases, these drugs afford only a modest degree of control while the side effects of these agents severely restrict their usefulness. Patients with nodulocystic acne suffer from large, inflammatory, suppurative nodules appearing on the face, and frequently the back and chest. In addition to their appearance, the lesions are tender and often purulently exudative and hemorrhagic. Disfiguring scars are frequently inevitable.

Therapies for acne involves local and systemic administration of vitamin compounds, collectively known as retinoids. Topical application of all-trans-retinoic acid has been tried with some success, particularly against comedones or blackheads, but this condition frequently returns when the treatment is withdrawn. (All-trans-retinoic acid is also known as tretinoin. These terms are used interchangeably throughout this specification.) Additionally, retinoic acid applied topically can be highly irritating and its use can be painful for the patient depending on the concentration used and the frequency of application.

A number of side effects complicates the administration of large doses of vitamin A. Among the many symptoms of hypervitaminosis A are weight loss, desquamation of the skin, hair loss, irritation of the oral and pharyngeal mucosa, and nose bleeds, headaches, bone pain, liver toxicity due to storage of vitamin A in the liver, papilledena, pseudotumor cerebri, demineralization and periosteal thickening of bones. Because of these and other side effects of oral treatment with vitamin A and all-trans-retinoic acid, which produces similar side effects, is rarely recommended for dermatopathic conditions.

The present invention relates to 13-cis-retinoic acid esters which are effective in the treatment of acne and other skin disorders when administered either topically and which show few if any side effects.

2. Description of the Prior Art

The successful use of 13-cis-retinoic acid, administered orally, for the treatment of cystic and conglobate acne was reported in Peck, et al., "Prolonged Remissions of Cystic and Conglobate Acne with 13-cis-Retinoic Acid," New Eng. J. Med. 300: 329–333 and 30: 359–360, Feb. 15, 1979. (13-cis-retinoic acid is also known as isotretinoin. These terms are used interchangeably throughout this specification.) In this study, a four month course of therapy with oral 13-cis-retinoic acid was begun at a minimum divided dosage of 1.0 mg per kilogram of body weight per day. The dosage was then increased in increments of 0.5 to 1.0 mg/kg/day at intervals of two to four weeks until either an appreciable therapeutic effect or dose-limiting toxicity was observed.

A report of the above study is also found in Gunby, "Synthetic Retinoid Used in Dermatopathies," J.A.M.A. 240: 610, Aug. 18, 1978. In this report, it is further stated that the oral dosages used were from 80 to 240 mg/day of 13-cis-retinoic acid in capsule form with an average dose of 140 mg/day. Still another report of this study will be found in Peck, et al., "Treatment of Darier's Disease, Lamellar Ichthyosis, Pityriasis Rubra Pilaris, Cystic Acne and Basal Cell Carcinoma with Oral 13-cis-Retinoic Acid," Dermat. 157 (Supp. 1): 11–12 (1978).

Belgian Patent No. 762,344 of Aug. 2, 1971, also discloses the use of orally administered 13-cis-retinoic acid for the treatment of acne (unspecified) and psoriasis. However, only a general dosage for various vitamin A compounds of from 0.1 mg to 0.5 mg to about 3.0 mg per kilogram of body weight is disclosed. Moreover, there is no example directed towards the use of 13-cis-retinoic acid.

In "Investigational Drug Brochure R04-3780," printed by Hoffman-LaRoche Inc., there appear several general statements indicating that all-trans-retinoic acid had been used for oral treatment of acne, and that 13-cis-retinoic acid had been proved to be less toxic than all-trans retinoic acid in animal experiments. There is also the statement that: "Skin diseases characterized by accelerated or pathological keratinization may respond to treatment with R04-3780 (sic: 13-cis-retinoic acid), . . . as well as acne." However, dosages were not discussed.

In a later edition of "Investigational Drug Brochure R04-3780", Feb. 1978, It is disclosed that interest in the therapeutic applications of 13-cis-retinoic acid developed when preliminary testing indicated that it had epithelium-protecting ability equivalent to retinoic acid and was apparently less toxic. There is a further disclosure of the treatment of an unspecified acne with 13-cis-retinoic acid administered orally, but with no indication of the method of varying dosage which is the subject of this invention.

The "Handbook of Nonprescription Drugs," 5th ed., 1977, A.P.A. pub., Pp 140, 319, 320, discloses the use of vitamin A and retinoic acid, but not the 13-cis-stereoisomer, in the treatment of acne (unspecified). However, the disclosure of this publication is opposite to that of the subject invention, in that it states: "The systemic use of vitamin A for the treatment of acne, . . . is not warranted by clinical evidence." at page 140; and that: "Treatments that have been abandoned or have not been proved effective include oral vitamin A, . . ." at page 320.

J. V. Straumford reported a systemic usage of large oral doses of retinol, the alcohol form of vitamin A, over a long period of time for the treatment of acne (Straumford, J. V., "Vitamin A: Its Effect on Acne," Northwest Med., 42: 219–255, August, 1943). These results, however, have been disputed and systemic therapy of acne utilizing retinol has been challenged by other investigators (Anderson, J. A. D., et al., "Vitamin A in Acne Vulgaries," Brit. Med. J., 2: 294–296, August, 1963; Lynch, F. W., et al., "Acne Vulgaris Treated with Vitamin A," Arch. Derm. 55: 355, 357, March 1947; and Mitchell, G. H., et al., "Results of Treatment of Acne Vulgaris by Intramuscular Injections of Vitamin A," Arch. Derm. 64: 428–434, October, 1951).

Topical administration of retinoic acid for the treatment of acne was reported by Kligman, et al., (Arch. Derm. 99: 469–476, 1969, U.S. Pat. No. 3,729,568). The effectiveness of this treatment as disclosed by Kligman is often associated with a noticeable irritating effect of topically applied retinoic acid.

Esters and amides of trans-retinoic acid which are useful for the treatment of acne are claimed in U.S. Pat. Nos. 4,055,659 (all trans-retinoyloxyacetamide) 4,126,697 (4-(all-trans-rentinoyloxyacetyl)-catechol), 4,126,698 (2-hydroxyethyl all-trans-retinoate) and 4,304,787 (benzyl all-trans-retinoate). All four of these patents to Gander, et al. also disclose mixed 2-hydroxy-1-propyl and 1-hydroxy-2-propyl all-trans-retinoates, N-(3,4-methylenedioxyphenylmethyl) all-trans-retinamide, and 4-nitrobenzyl all-trans-retinoate. The effectiveness of all these compounds was shown through testing which measured increase in DNA synthesis in epidermal cells. This ability has been associated with the effectiveness of retinoic acid in the treatment of acne. See, for example, Christophers and Braun-Falco, "Stimulation of Epidermal DNA-Synthesis with Vitamin A-Acid," Arch. Klin. exp. Derm. 232: 427–433 (1968) and Wolfe, et al., "Changes in Epidermal Differentiation After Vitamin A Acid," Arch. Klin. exp. Derm. 237: 744–795 (1970). No claim is made and no testing is disclosed in the Gander, et al. patents which indicates that the esters or amides show fewer or greater side effects than trans-retinoic acid.

The process for treating acne vulgaris topically utilizing retinal, the aldehyde form of vitamin A, is disclosed in U.S. Pat. No. 3,932,665. The aldehyde form, unlike the acid form of vitamin A, exerts its therapeutic effect without producing irritation, inflammation, erythema, or peeling of the skin. This patent also discloses the topical use of 13-cis-retinal in the treatment of acne vulgaris.

The method of treating acne with C-20 and C-22 vinylogs of desmethyl retinoic acid is disclosed in U.S. Pat. No. 3,882,244. These vinylogs as disclosed in the patent are applied topically to the site of the acne infection as a solution, ointment or powder. The treatment of acne vulgaris with retinoic acid analogs particularly 11-(2',6',6'-trimethylcyclohex-1'-enyl-1')-5,9-dimethylundeca-2,4,6,8,10-pentenoic acid is disclosed in U.S. Pat. No. 3,934,028. This compound can be used either internally or topically. When taken orally, the daily dosage of this compound ranged from 30–300 mg taken over from 2 to 8 weeks. However, there is no indication that the compound leads to remission from the disease after administration of the compound is withdrawn.

Although 13-cis-retinoic acid is generally less toxic than all-trans retinoic acid, there are still precautions that must be observed in its use. With oral retinoic acid, headaches, nausea, vomiting, and some of the skin and mucous membrane lesions experienced with hypervitaminosis A have been reported. Because of chemical and pharmacological similarities between 13-cis-retinoic acid, retinoic acid and retinol, similar adverse reactions occur with 13-cis-retinoic acid. See Blackman, et al., "Blepharoconjunctivitis: Side Effect of Oral 13-cis-Retinoic Acid Therapy of Dermatologic Disease," Ophthal. 85: 35, July 1978, and some of the above articles.

An improved method of treating nodulocystic and conglobate acne in human beings by oral administration of 13-cis-retinoic acid in amounts and for periods of time which afford an effectively complete remission from the condition even after administration of the compound ceases is disclosed in U.S. Pat. No. 4,322,438 to Peck.

The improvement over the prior art, was the use of a "high-low" oral dosage schedule, which proved effective in the treatment of cystic acne, while reducing the toxic effects of the 13-cis-retinoic acid. Further studies, (Jones, H., et al., "13-cis-Retinoic Acid and Acne," The Lancet, 1048, Nov. 15, 1980) however, have indicated that there are dose related side effects associated with the use of 13-cis-retinoic acid, particularly dryness of the skin and mucous membranes. More seriously, 13-cis-retinoic acid, which is marketed as an oral acne drug under the trademark Accutane ® (isotretinoin/Roche), can cause serious birth defects. It also has a few other serious short-term side effects, such as increased pressure in the brain, clouding of the cornea and inflammation of the intestines. Physician's Desk Reference, at 1665–1667 (39th ed. 1985). Other drugs presently used in the treatment of acne include benzoyl peroxide, tretinoin (all-trans-retinoic acid, Retin-A-Ortho), clindamycin, tetracycline, erythromycin, minocycline, and estrogens (for females).

Benzoyl peroxide is considered safe and effective in mild and moderate acne treatment. Tretinoin is effective but has the previously mentioned deleterious side effects, as well as accelerating photocarcinogenesis. The antibiotics are reasonably effective but have side effects such as gastrointestinal problems including reports of pseudomembranous colitis. Estrogens are sometimes effective in treating acne, but the side effects of these drugs make them less than desirable.

Isotretinoin is the most dramatic and exciting breakthrough for the treatment of severe acne (Pochi, P. E., "Oral Retinoids in Dermatology," Arch. Dermatolo., 118: 57–61 (1982). The fact that it is irritating when applied topically (Popovich and Sperandio, "Current Topical Acne Therapy," Pharmacy Times, June, 104–115 (1984) and causes birth defects when administered orally (Robinson, "Isotretinoin," Drugs of Today, XVIII, 12: 642–649 (1982), however, prompted the present inventors to explore the possibility of inventing a prodrug of isotretinoin that would (1) be applied topically, (2) be absorbed by human skin, (3) be effective in the treatment of acne, and (4) be safe.

Also, since there is some indication that isotretinoin achieves remission in rosacea, gram-negative folliculitis, seborrhea, and keratinizing dermatoses (Bollag, "The Development of Retinoids in Experimental and Clinical Oncology and Dermatology," J. Amer. Acad. of Derm., 9: 797–805 (1983), it is reasonable to assume that the prodrugs of the present invention may be effective in the topical treatment of these skin disorders.

Finally, since the aromatic analog of retinoic acid, etretinate (Tigason-Roche) is effective in the oral treatment of severe psoriasis (Kaplan et al., "Etretinate Therapy for Psoriasis: Clinical Responses, Remission Times, Epidermal DNA and Polyamine Responses," J. American Acad. of Derm., 8: 95–102 (1983), topical retinoids might have an advantageous therapeutic index compared with drugs currently in use.

The present inventors are working under the hypothesis that topical administration of the drug of the present invention will result in less systemic toxicity compared with oral administration.

A topical prodrug that would retain the effectiveness of isotretinoin and would be essentially free of the deleterious side effects of isotretinoin would provide a much needed solution to a widespread problem.

SUMMARY OF THE INVENTION

This invention is directed to novel derivatives of cis-retinoic acid which are useful in the treatment of acne but which minimize the toxic side-effects associated with cis-retinoic acid treatments of acne.

The derivatives have the formula:

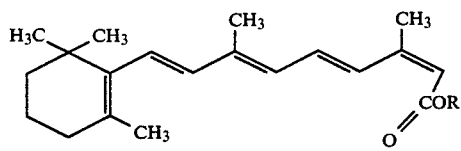

wherein R is

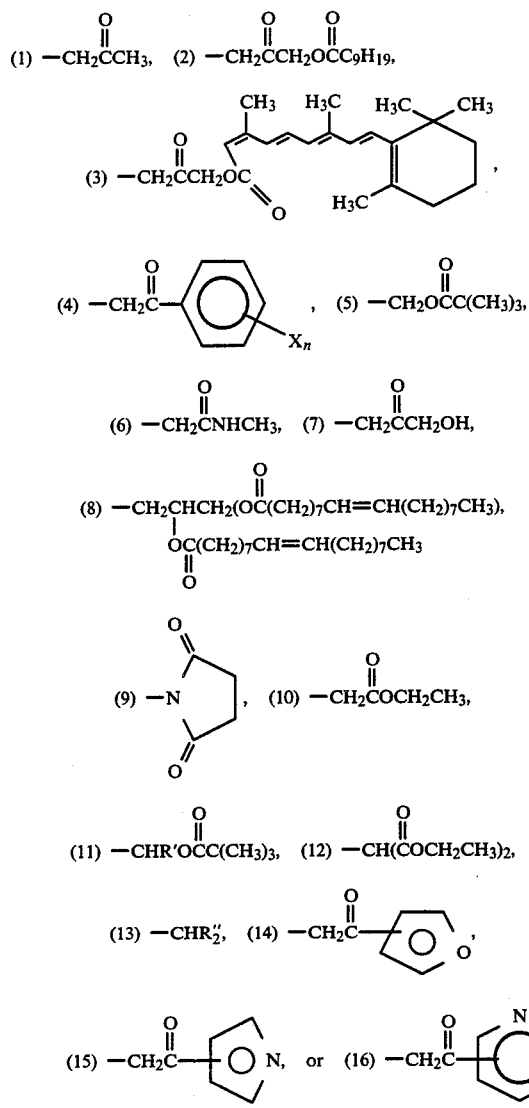

wherein X is —H, —F, —Cl, —Br, —I, —OH, —OR',

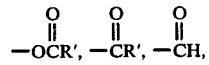

—CN, —NO$_2$, —NH$_2$, —NHR', or —NR'$_2$; wherein n is a number from 1 to 5; wherein R' is a member of the group consisting of lower alkyls ranging from C$_1$ to C$_6$; and wherein R" is a member of the group consisting of

—OR',

and —R'.

These derivatives can be applied topically or orally without causing irritation or with less irritation than found with state of the art treatments, and are an effective and safe treatment for acne.

While it is believed that these compounds are useful for the treatment of acne, it is also suggested that they are useful for treatment of amelioration of the same additional classes of skin disorders as is retinoic acid itself. These disorders include ichthyoses (e.g., ichthyosis hystrix, epidermolytic hyperkeratosis, and lamelar ichthyosis), follicular disorders (e.g., pseudofolliculites, senile comedones, nevus comidonicas, and trichostatis spinulosa), benign epithelial tumors (e.g., flat warts, trichoepithelioma, and molluscum contagiosum), perforated dermatoses (e.g., elastosis perforans seripiginosa and Kyrle's disease), and disorders of keratinization (e.g., Darier's disease, keratoderma, hyperkeratosis plantaris, pityriasis rubra pilaris, lichen planus, acanthosis nigricans, and psoriasis).

TOPICAL ASSAY

A topical assay to test for pseudocomedone (utriculus) reduction in the rhino mouse was conducted.

Each test compound and a vehicle control was applied topically to the dorsal trunk of the rhino mouse. The utriculus diameters were measured with an ocular micrometer. The assay is unique and proprietary to Ortho Pharmaceutical Corp. and is based upon the work of Kligman, et al. (1979) and Van Scott (1972). Kligman, et al., "The Effect on Rhino Mouse Skin of Agents which Influence Keratinization and Exfoliation," J. Invest. Derm. 73: 354–358 (1979). Van Scott, "Experimental Animal Integumental Models for Screening Potential Dermatologic Drugs," in *Pharmacology of the Skin*, eds. Montagna, et al., New York, Appleton-Century-Crofts, 1972, pp. 523–533. Mann, "Hair Loss and Cyst Formation in Hairless and Rhino Mutant Nice," Anat. Rec. 170: 485–500 (1971). Mezick, et al., "Topical and Systemic Effects of Retinoids on Horn-Filled Utriculus Size in the Rhino Mouse. A Model to Quantify Antikeratinizing "Effects of Retinoids," J. Invest. Derm. 83: 110–113 (1984). Mezick, et al., "Anti-Acne Activity of Retinoids in the Rhino Mouse," in *Models in Dermatology*, eds. Maibach et al., Basel, Karger, 1985.

The dorsal trunk of the rhino mouse was the test site. Each test compound was dissolved in alcohol:propylene glycol (70:30, v/v) or other suitable vehicle and topically applied (0.1 ml) to the dorsal trunk once daily, five consecutive days/week for two weeks. Also, administration could be oral i.p. in a suitable vehicle. Following treatment, the animals were sacrificed by cervical dislocation. The treated dorsal trunk skin was removed from the animal and placed into 0.5% acetic acid for up to 18 hours at approximately 4° C. After this, the epidermis with the "acne cysts" was separated from the underlying dermis. The sheets of epidermis were processed by routine methods to permanent whole mounts for microscopic examination. Also, full-thickness samples could be taken, stained (H&E) and examined by light microscopy.

The utriculus diameters were measured with an ocular micrometer to compare effects of test compounds to vehicle control and/or reference compound on cyst reduction. Light microscopy was used to determine effects on cell differentiation. The results are summarized in Table 1:

TABLE 1

TOPICAL RHINO MOUSE ASSAY

| RETINOID | % CONCENTRATION | % UTRICULUS REDUCTION |
|---|---|---|
| Cpd. 3 | 0.1 | 23.7 |
| Cpd. 2 | 0.1 | 52.2 |
| Cpd. 1 | 0.1 | 57.7 |
| 13-cis-retinoic acid | 0.1 | 56.3 |
| all trans retinoic acid | 0.1 | 65.9 |

A second topical assay was conducted following the procedure described above. All-trans-retinoic acid was used as a control. Cpd. 1, Cpd. 4 wherein X is H (Cpd. 4), Cpd. 4 wherein X is para-methoxy (Cpd. 4 —OCH$_3$), Cpd. 4 wherein X is para-F (Cpd. 4-F) and Cpd. 10 were tested. Cpd. 10 has the formula:

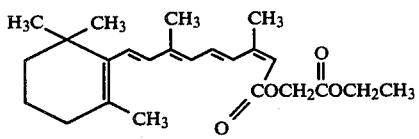

The results are summarized in Table 2:

TABLE 2

TOPICAL RHINO MOUSE ASSAY

| RETINOID | % CONCENTRATION | % UTRICULUS REDUCTION |
|---|---|---|
| Cpd. 1 | 0.1 | 63.2 |
| Cpd. 4 | 0.1 | 53.2 |
| Cpd. 4-OCH$_3$ | 0.1 | 56.8 |
| Cpd. 4-F | 0.1 | 55.3 |
| Cpd. 10 | 0.1 | 55.7 |
| all trans | 0.1 | 75.8 |

ORAL ASSAY

An oral assay for hamster sebaceous gland reduction was conducted.

Hamsters were dosed orally with the test compound and vehicle alone. The reduction in sebaceous gland size was estimated microscopically in relation to the control. The assay is unique and proprietary to Ortho Pharmaceutical Corp. and is based upon the work of Plewig et al. (1977) and Gomex et al. (1980). Plewig, et al., "Hamster Ear Model for Sebaceous Glands," J. Invest. Derm. 68: 171–176 (1977). Gomez, et al., "Effect of 13-cis-Retinoic Acid on the Hamster Flank Organ," J. Invest. Derm. 74: 392–397 (1980).

For oral (p.o.) studies, male Syrian golden hamsters were dosed at 5 ml/kg, once daily, five consecutive days/week for two or three weeks. Modified but similar dosing schedules could be used. Control hamsters were dosed with vehicle alone at 5 ml/kg. Following final treatment (up to 72 hours), the hamsters were sacrificed in a CO$_2$ atmosphere. Samples of each test site were placed into 10% buffered formalin and histologically prepared. Serial sections of each sample were stained (H&E) and examined microscopically.

The reduction in sebaceous gland size was subjectively estimated microscopically in relation to the control treated sites. To quantify sebaceous gland size, cross-sectional areas were measured with an image analyzer system. The results are summarized in Table 3:

TABLE 3

ORAL HAMSTER SEBACEOUS GLAND ASSAY

| RETINOID | DOSE (mg/kg) | % SEBACEOUS GLAND REDUCTION |
|---|---|---|
| Cpd. 3 | 32 | 29.1 |
| Cpd. 2 | 32 | 22.7 |
| Cpd. 1 | 32 | 68.8 |
| 13-cis-retinoic acid | 10 | 43.4 |
| 13-cis-retinoic acid | 32 | 74.6 |

From the results it can be seen that the compounds of the invention were as effective as 13-cis-retinoic acid in both topical and oral applications. The data presented is raw data which does not take into account the differences in molecular weight between the compounds of the invention and 13-cis- or all-trans-retinoic acid. If one does take this into account, as must be done to accurately compare the activity of the various compounds, it can be seen that many of the compounds of this invention are equally or more effective than either 13-cis- or all-trans-retinoic acid. A further advantage of the compounds of the invention over 13-cis-retinoic acid, is their non-irritating characteristics when applied topically. This highly desirable characteristic is not seen when 13-cis-retinoic acid is used.

The compounds of the invention may be topically applied to the acne site in any suitable pharmaceutically-acceptable vehicle, as for example a liquid carrier such as propylene glycol-ethanol, propylene glycol-ethanolchloroform, and the like. A preferred liquid composition is a solution of a small amount of at least one of the compounds of the invention in a combination of (A) from about 25% to about 75% by weight of 95% ethanol and (B) from about 75% to about 25% by weight of a liquid glycol. A typical solvent carrier of this type comprises 70% by weight 95% ethyl alcohol and 30% by weight propylene glycol. The preferred concentration of the active compound in these compositions is at least about 0.01% by weight, more preferably from about 0.01% to about 0.5% by weight, and most preferably from about 0.05% to about 0.2% by weight, but any therapeutically effective concentration may be used. This method of use is similar to the method taught in U.S. Pat. No. 3,729,568. These compositions and the method of treating acne by topical application to the acne site of at least one of the compounds of the invention are considered part of the present invention. Although topical application of the compounds of the invention is the preferred method of application, oral dosages of the compound of the present invention appear to be effective, based on the hamster studies discussed previously (ORAL ASSAY).

The preparation of the compounds of the present invention is illustrated by the following examples.

EXAMPLE 1

Synthesis of Compound 1

1-(13-cis-retinoyloxy)-2-propanone

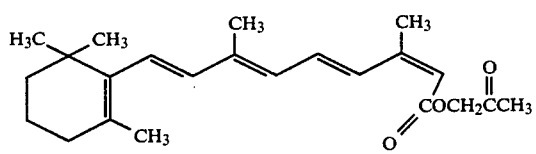

Into a 100 ml round bottom flask was added 1.0 g (0.0033 mole) of isotretinoin, 25 ml of anhydrous methanol, 0.2 g (0.0035 mole) of KOH. The solution was stirred at room temperature until the isotretinoin dissolved. After the solvent was removed under vacuum, 25 ml of acetonitrile was added and the solution was again concentrated to a semisolid under vacuum. Chloroacetone (2.0 g, 0.032 mole), 0.1 g 18-crown-6 (0.00038 mole), and 100 ml of acetonitrile was added. The solution was stirred for 6 hrs. at room temperature with a magnetic stirrer. The sample was concentrated to about 5 ml and chromatographed on a neutral aluminum oxide (Aldrich #19,997-4) column (14×1.8 cm). The sample eluted quickly and the vast majority of impurities remained on the column. The sample was eluted stepwise with 100 ml of 20% dichloromethane in hexane, 100 ml of 50% dichloromethane in hexane, 100 ml of dichloromethane, 100 ml of 10% ethyl acetate in dichloromethane, and finally with 200 ml of 25% ethyl acetate in dichloromethane. Fractions of 25 ml were collected and evaluated by TLC on silica gel (EM Reagents #5775) developed with ethyl acetate/heptane ¼. The fractions containing the product were combined and concentrated to give an orange oil which solidified on cooling to give 0.88 g (74% yield) mp 66°-68°. Triturating the sample with 2×2 ml of cold hexane gave a homgeneous product, mp 73°-74°, mp of isotretinoin is 174°-175° (Merck Index, 10th Ed). TLC on silica gel developed with ½ ethyl acetate/heptane showed one spot, Rf—0.56; however, isotretinoin also has Rf=0.56. TLC on aluminum oxide (EM Reagents #5581) showed the sample to be homogeneous. These plates developed with ¼ ethyl acetate/heptane to give Rf=0.53, isotretinoin has Rf=0.0. The sample can be recrystallized from hexane but requires weeks for recrystallization to be complete. NMR (CDC13) spectrum of Compound 1 was identical to the spectrum of isotretinoin except for two additional peaks and the lack of a carboxylic acid peak. The two additional peaks were at 4.5 ppm (singlet, 2 protons, —OCH₂CO—) and 2.1 ppm (singlet, 3 protons, —COCH₃).

EXAMPLE 2

Synthesis of Compound 2

1-(13-cis-retinoyloxy)-3-decanoyloxy-2-propanone

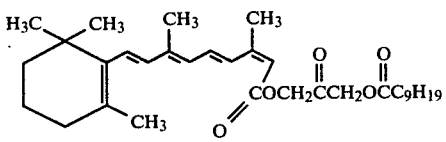

The following synthetic scheme was used for the synthesis of Cpd. 2.

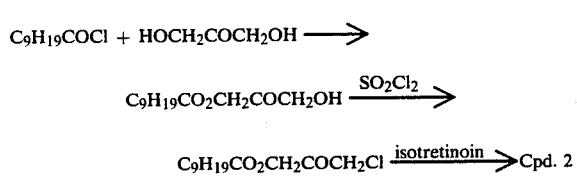

Into a 500 ml round bottom flask fitted with a reflux condensor and magnetic stirrer was added 20 g (0.22 mole) of dihydroxyacetone dimer, 300 ml of acetone, 30 ml of DMF, and 30 ml of pyridine and 14 g (0.078 mole) of decanoyl chloride. The dihydroxyacetone dimer dissolved as the acid chloride was added. The solution was refluxed for 30 min. and then stirred for 1 hr. The reaction was poured into 2 l of cracked ice and allowed to stand for 2 hrs. as the product crystallized. The solid was collected, dissolved in dichloromethane and dried (Na₂SO4). The solid contained large quantities of water which had to be removed. The dichloromethane was removed under vacuum and the oil was dissolved in acetone and placed in the freezer (−10°) overnight. The disubstituted dihydroxyacetone impurity separated and was removed. Sufficient water was added to make the solution about 25% water by volume and after standing overnight in the freezer, the product separated and was recrystallized from dichloromethane/hexane to give 5.2 g, mp 91°-93° C. TLC on silica gel developed with 4/1 heptane/ethyl acetate, visualized with iodine, showed the product to be homogeneous. NMR (CDC13/DMSO-D6) showed the correct ratio for —OCH₂COCH₂— protons to C₉H₉— protons. The NMR spectrum was complex as is the NMR spectrum of dihydroacetone. Into a 100 ml round bottom flask equipped with a reflux condenser and a magnetic stirrer was added 2.5 g (0.01 mole) of the above alcohol and 15 ml of thionyl chloride. The solution was refluxed for 70 min and the unreacted thionyl chloride was removed under vacuum. Toluene, 25 ml, was added and removed under vacuum to remove the last traces of thionyl chloride. The remaining oil solidified on cooling and was recrystallized from 15 ml of hexane to give 1.45 g (54% yield) mp 40°-41°. NMR (CDC13) 4.7 ppm (singlet, 2 protons, —CO₂CH₂CO—), 4.0 ppm (singlet, 2 protons, —COCH₂Cl), 2.35 ppm (triplet, 2 protons, C₈H₁₇CH₂CO—), 1.2 ppm (singlet, 14 protons, H₃C(CH₂)₇CH₂—), 0.85 ppm (triplet, 3 protons, H₃C(CH₂)₇—).

The coupling of the alkyl chloride to isotretinoin was carried out as described for Cpd. 1. Cpd. 2 was a low melting solid (mp about 10°-15°). Using equal molar concentration of the above chloro compound and isotretinoin a yield of 41% can be obtained. TLC indicates the sample to be homogenous. Using the same conditions as described for Cpd. 1, on silica gel Rf=0.69 and on aluminum oxide Rf=0.37. The NMR spectrum of the product was essentially the combined spectra of the two reagents, isotretinoin and the substituted chloromethyl ketone, which are coupled to give Cpd. 2. There was one minor change, however. The peak, at 4.0 ppm (—COCH2Cl) had disappeared and the methylene hydrogens (of —COCH2Cl) had shifted to 4.5 ppm where 2 singlets appeared and were separated by about 0.02 ppm (4 protons, —CO2CH2COCH2OCO—).

EXAMPLE 3

Synthesis of Compound 3

1,3-bis-(13-cis-retinoyloxy)-2-propanone

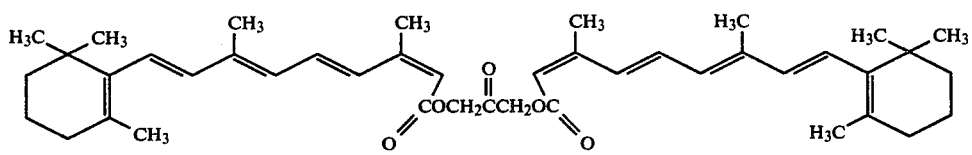

The procedure for Cpd. 1 was used for Cpd. 3 with minor changes. Instead of chloroacetone, 1,3-dichloroacetone (0.2 g, 0.0016 mole) was used. The solution was stirred for 24 hrs. before chromatography. The reaction was worked up as described for Cpd. 1 to give 1.41 g (38% yield) mp 81°–85°. After triturating with 2×2 ml hexane the melting point increased to 100°–102°. TLC indicated sample to be homogenous. Using the same conditions as described for Cpd. 1, on silica gel Rf=0.67 and on aluminum oxide Rf=0.42. NMR (CDC13) spectrum of Cpd. 3 was identical to the spectrum of isotretinoin except for the additional peak at 4.55 ppm (singlet, 2 protons, —OCH2CO—).

EXAMPLE 4

Synthesis of Compound 4

13-cis-retinoyloxy methyl phenyl ketone

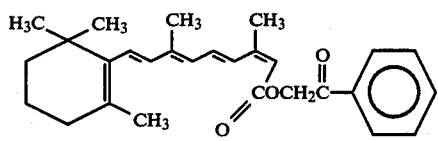

The procedure for Cpd. 1 is used for Cpd. 4 with minor changes. Instead of chloroacetone, α-chloroacetophenone is used.

Cpd. 4 is similar to Cpd. 1, except that the terminal methyl group has been replaced with a phenyl group. This will allow molecular modification by phenyl group substitution in order to spread the physicochemical properties of the derivatives for Quantitative Structure-Activity Relationship (QSAR) studies (Purcell et al., "Strategy of Drug Design: A Molecular Guide to Biological Activity," Wiley, New York, 1973).

EXAMPLE 5

Synthesis of Compound 5

13-cis-retinoyloxymethyl 2,2-dimethylpropanoate

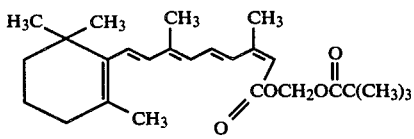

The procedure for Cpd. 1 is used for Cpd. 5 with minor changes. Instead of chloroacetone, chloromethyl pivalate is used.

Cpd. 5 uses the same ester derivative as the antibiotic prodrug pivampicillin in which the acyloxymethyl ester is hydrolyzed by non-specific esterases to generate ampicillin (Sinkula, "Application of the Pro-Drug Approach to Antibiotics," in "Pro-drugs as Novel Drug Delivery Systems," ACS Symposium Series (1974), p. 116–153).

EXAMPLE 6

Synthesis of Compound 6

2-(13-cis-retinoyloxy)-N-methyl-acetamide

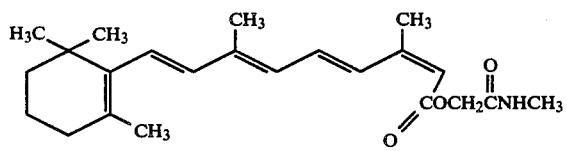

The procedure for Cpd. 1 is used for Cpd. 6 with minor changes. Instead of chloroacetone, N-methyl chloroacetamide is used.

Cpd. 6 is designed to explore hydrophilicity: the N-methyl acetamide group is very hydrophilic (Wolfenden, "Waterlogged Molecules," Science, 222: 1087–1093 (1983)).

EXAMPLE 7

Synthesis of Compound 7

1-(13-cis-retinoyloxy)-3-hydroxy-2-propanone

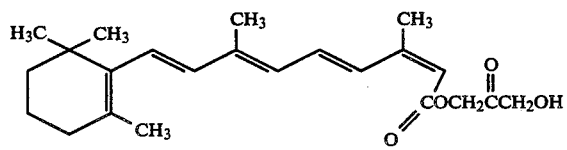

Cpd. 7 is prepared by reacting the acid chloride of isotretinoin with an excess of dihydroxyacetone. State of the art synthetic schemes are available (Haslam, "Recent Developments in Methods for the Esterification and Protection of the Carboxyl Group," Tetrahedron, 36: 2409–2433 (1980)) and can also be used as an alternative.

Cpd. 7 is similar to Cpd. 1 with a terminal methyl hydroxyl group instead of a methyl group. This modification should make Cpd. 7 more "glyceride-like" and more hydrophilic.

EXAMPLE 8

Synthesis of Compound 8

1-(13-cis-retinoyloxy)-2,3-dioleoylpropane

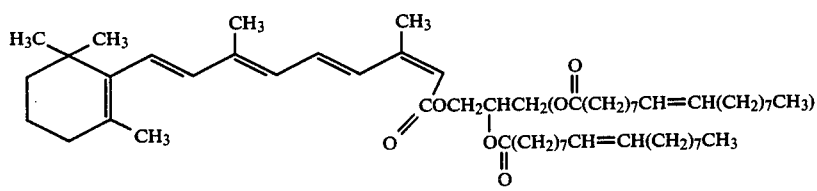

Cpd. 8 is prepared by reacting oleoyl chloride with glyceraldehyde followed by reduction of the aldehyde group with sodium borohydride. This gives a 1,2-disubstituted glyceride with an available hydroxyl for coupling. The coupling of isotretinoin is carried out as for Cpd. 7. This scheme is based on the synthetic procedure for glyceride derivatives of aspirin (Paris, et al., "Glycerides as Prodrugs. 2. 1,3-Dialkanoyl-2-(2-methyl-4-oxo-1,3-benzodioxan-2-yl) glycerides (Cyclic Aspirin Triglycerides) as Antiiflammatory Agents," J. Med. Chem., 23: 79–82 (1980)).

Cpd. 8 is based on evidence that topical application of glycerides is an effective means of incorporating essential fatty acids into the skin (Prottery, et al., "The Repair of Impaired Epidermal Barrier Function in Rats by the Cutaneous Application of Linoleic Acid," British J. of Derm., 94: 13–21, (1976)).

EXAMPLE 9

Synthesis of Compound 9

Succinimdyl 13-cis-retinoate

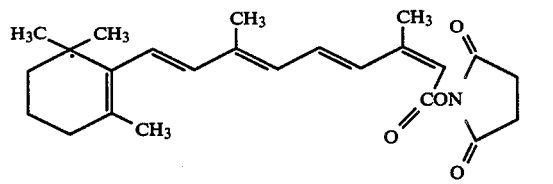

Cpd. 9 is synthesized by coupling isotretinoin with N-hydroxysuccinimide (Zimmerman, et al., "The Effect of Active Ester Components on Racemization in the Synthesis of Reptiles by the Dicyclohexyl-carbodiimide Method," J. Am. Chem. Soc., 89: 7151–7152 (1967)).

Cpd. 9 is the most easily hydrolyzed prodrug. The N-hydroxy-succinimide group gives an activated ester linkage and is used in peptide synthesis because of this property.

The above examples have been provided to illustrate the present invention, the scope of which is defined by the following claims:

What is claimed is:

1. A compound of the formula:

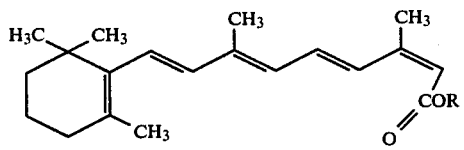

wherein R is a member of the group consisting of:

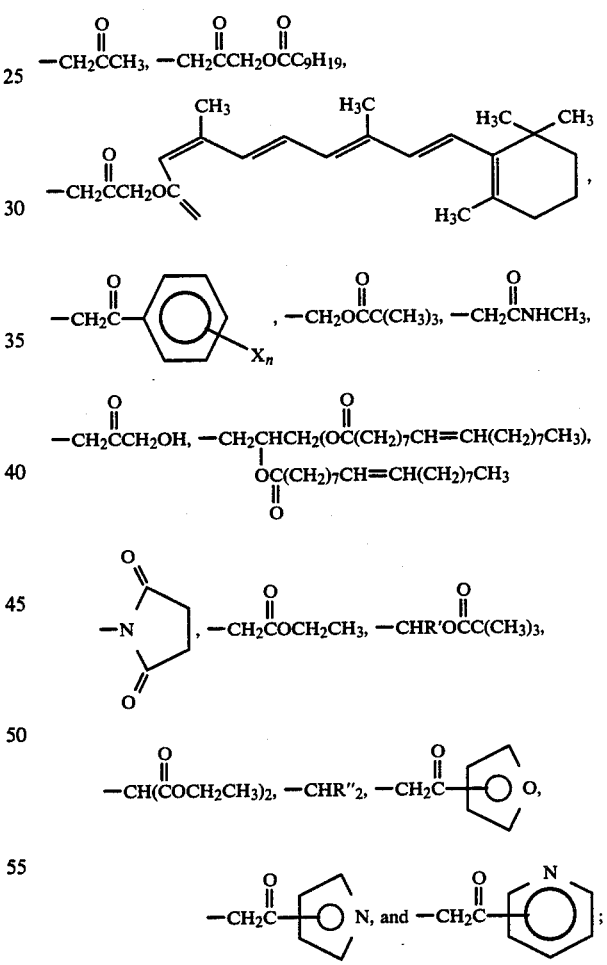

wherein X is a member of the group consisting of:
—H, —F, —Cl, —Br, —I, —OH, —OR′, —OCR′, —CR′, —CH, (each with =O)

—CN, —NO$_2$, —NH$_2$, —NHR′, and —NR′$_2$;
wherein n is a number from 1 to 5;

wherein R' is a member of the group consisting of lower alkyls ranging from $C_1$ to $C_6$; and p1 wherein R" is a member of the group consisting of:

$$-O\overset{O}{\underset{\|}{C}}R',$$

—OR', $$-\overset{O}{\underset{\|}{C}}R',$$

and —R'.

2. The compound of claim 1, having the formula:

[Structure: β-ionone ring with polyene chain terminating in $-COCH_2\overset{O}{\underset{\|}{C}}CH_3$, with $H_3C$, $CH_3$ on ring, $CH_3$ on ring, and $CH_3$, $CH_3$ on chain]

3. A pharmaceutical composition for the treatment of acne which comprises:
an effective acne-treatment amount of an acne-treating compound of the formula:

[Structure: β-ionone ring with polyene chain terminating in COR]

wherein R is a member of the group consisting of:

$$-CH_2\overset{O}{\underset{\|}{C}}CH_3, \quad -CH_2\overset{O}{\underset{\|}{C}}CH_2O\overset{O}{\underset{\|}{C}}C_9H_{19},$$

$$-CH_2\overset{O}{\underset{\|}{C}}CH_2O\overset{O}{\underset{\|}{C}}-\text{[retinyl chain with ring]},$$

$$-CH_2\overset{O}{\underset{\|}{C}}-\text{[phenyl]}-X_n, \quad -CH_2O\overset{O}{\underset{\|}{C}}C(CH_3)_3, \quad -CH_2\overset{O}{\underset{\|}{C}}NHCH_3,$$

$$-CH_2\overset{O}{\underset{\|}{C}}CH_2OH, \quad -CH_2CHCH_2(O\overset{O}{\underset{\|}{C}}(CH_2)_7CH=CH(CH_2)_7CH_3),$$
$$\underset{O}{\overset{|}{O\underset{\|}{C}(CH_2)_7CH=CH(CH_2)_7CH_3}}$$

[succinimide structure: $-N$ with two C=O], $-CH_2\overset{O}{\underset{\|}{C}}OCH_2CH_3$, $-CHR'O\overset{O}{\underset{\|}{C}}C(CH_3)_3$, -continued $$-CH(\overset{O}{\underset{\|}{C}}OCH_2CH_3)_2, \quad -CHR''_2, \quad -CH_2\overset{O}{\underset{\|}{C}}-\text{[furan]}\, O,$$

$$-CH_2\overset{O}{\underset{\|}{C}}-\text{[pyrrole]}\, N, \text{ and } -CH_2\overset{O}{\underset{\|}{C}}-\text{[pyridine]}\, N;$$

wherein X is a member of the group consisting of:
—H, —F, —Cl, —Br, —I, —OH, —OR, —OR', $$-O\overset{O}{\underset{\|}{C}}R', \quad -\overset{O}{\underset{\|}{C}}R', \quad -\overset{O}{\underset{\|}{C}}H,$$

—CN, —$NO_2$, —$NH_2$, —NHR', and —$NR_2'$;
wherein n is a number from 1 to 5;
wherein R' is a member of the group consisting of lower alkyls ranging from $C_1$ to $C_6$; and
wherein R" is a member of the group consisting of $$-O\overset{O}{\underset{\|}{C}}R',$$

—OR', $$-\overset{O}{\underset{\|}{C}}R',$$

and —R';
admixed with a pharmaceutically-acceptable vehicle.

4. The composition of claim 3, wherein said acne-treating compound comprises from about 0.01% to about 0.5% by weight of said composition.

5. The composition of claim 3, wherein said acne-treating compound comprises from about 0.05% to about 0.2% by weight of said composition.

6. The composition of claim 3, wherein said vehicle is a mixture selected from the group consisting of propylene glycol-ethanol and propylene glycol-ethanol chloroform.

7. The composition of claim 3, wherein said acne-treating compound has the formula:

[Structure: β-ionone ring with polyene chain terminating in $-COCH_2\overset{O}{\underset{\|}{C}}CH_3$]

8. A method for treating acne in a subject requiring such treatment which comprises:
topical application to the acne site of said subject of a pharmaceutical composition which comprises an effective acne-treatment amount of a compound of the formula:

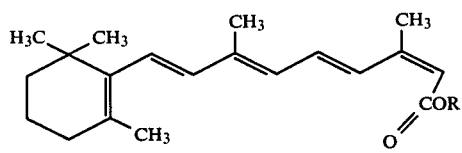

wherein R is a member of the group consisting of:

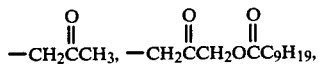

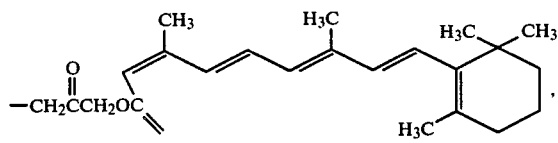

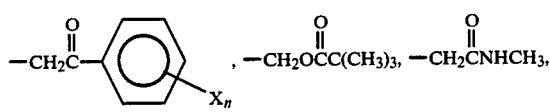

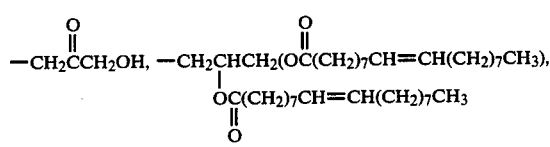

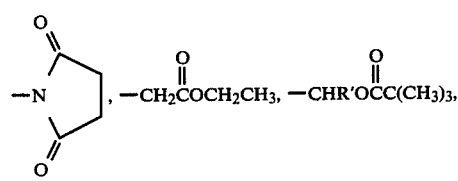

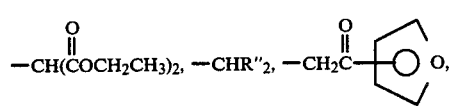

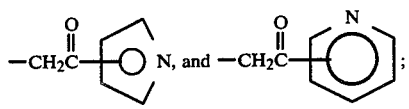

wherein X is a member of the group consisting of:
—H, —F, —Cl, —Br, —I, —OH, —OR, —OR',

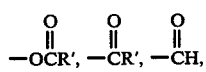

—CN, —NO$_2$, —NH$_2$, —NHR', and —NR$_2$';
wherein n is a number from 1 to 5;
wherein R' is a member of the group consisting of lower alkyls ranging from C$_1$ to C$_6$; and
wherein R" is a member of the group consisting of

—OR',

and —R';
admixed with a pharmaceutically-acceptable topical vehicle.

9. The method of claim 8, wherein said acne-treating compound comprises from about 0.01% to about 0.05% by weight of said composition.

10. The method of claim 8, wherein said acne-treating compound comprises from about 0.05% to about 0.02% by weight of said composition.

11. The method of claim 8, wherein said vehicle is a mixture selected from the group consisting of propylene glycol-ethanol and propylene glycol-ethanol chloroform.

12. The method of claim 8, wherein said acne-treating compound has the formula:

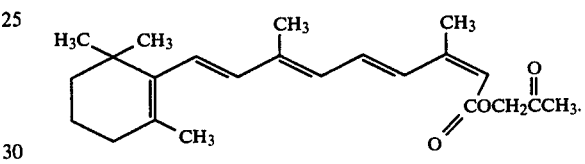

13. A method for treating acne in a subject requiring such treatment which comprises:
oral application to said subject of an effective acne-treatment amount of a compound of the formula:

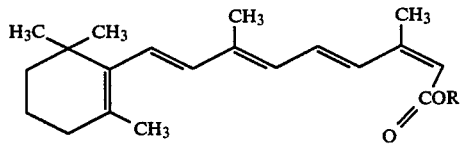

wherein R is a member of the group consisting of:

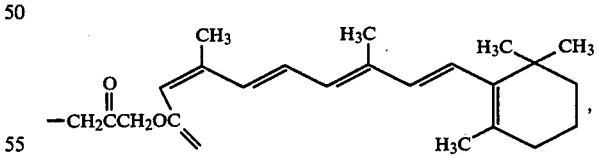

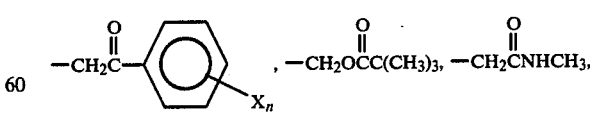

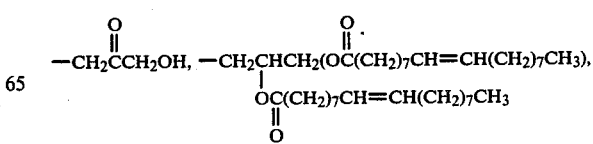

-continued

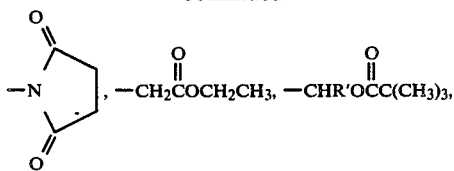

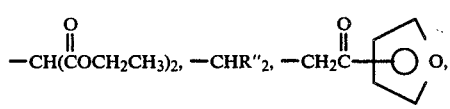

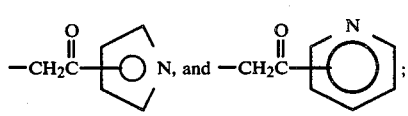

wherein X is a member of the group consisting of: —H, —F, —Cl, —Br, —I, —OH, —OR, —OR',

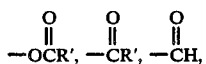

—CN, —NO$_2$, —NH$_2$, —NHR', and —NR$_2$';
wherein n is a number from 1 to 5;

wherein R' is a member of the group consisting of lower alkyls ranging from C$_1$ to C$_6$; and wherein R" is a member of the group consisting of

—OR',

and —R';
admixed with a pharmaceutically acceptable oral vehicle.

14. The method of claim 13, wherein said acne-treating compound has the formula:

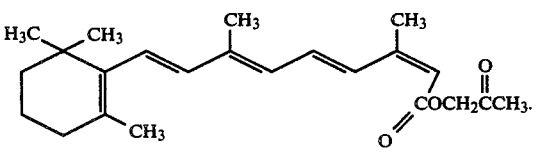

* * * * *